United States Patent
Elmaanaoui

(10) Patent No.: US 11,473,896 B2
(45) Date of Patent: Oct. 18, 2022

(54) COHERENCE RANGE IMAGING USING COMMON PATH INTERFERENCE

(71) Applicant: Canon U.S.A. Inc., Melville, NY (US)

(72) Inventor: Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 20 days.

(21) Appl. No.: 15/672,003

(22) Filed: Aug. 8, 2017

(65) Prior Publication Data
US 2018/0045501 A1   Feb. 15, 2018

Related U.S. Application Data

(60) Provisional application No. 62/374,324, filed on Aug. 12, 2016.

(51) Int. Cl.
*G01B 9/02* (2022.01)
*G01B 9/02091* (2022.01)
(Continued)

(52) U.S. Cl.
CPC ........ *G01B 9/02091* (2013.01); *A61B 5/0066* (2013.01); *G01B 9/0205* (2013.01); *G01B 9/02015* (2013.01); *G01B 9/02057* (2013.01)

(58) Field of Classification Search
CPC .............. G01B 9/02091; G01B 9/0205; G01B 9/02015; G01B 9/02057; A61B 5/0066
See application file for complete search history.

(56) References Cited

U.S. PATENT DOCUMENTS 4,627,731 A * 12/1986 Waters ...................... G01J 9/02
356/479
6,485,413 B1   11/2002 Boppart et al.
(Continued)

OTHER PUBLICATIONS

Utkarsh Sharma, et al., "Common-path optical coherence tomography with side-viewing bare fiber probe for endoscopic optical coherence tomography", Review of Scientific Instruments, American Institute of Physics, Melville, NY, US, vol. 78, pp. 113102-1-113102-4, No. 11, Nov. 6, 2007.
(Continued)

*Primary Examiner* — Hwa Andrew Lee
(74) *Attorney, Agent, or Firm* — Canon U.S.A., Inc. I.P. Division

(57) ABSTRACT

One or more devices, systems, methods and storage mediums for performing common path optical coherence tomography (OCT) with a controlled reference signal and efficient geometric coupling are provided. Examples of such applications include imaging, evaluating and diagnosing biological objects, such as, but not limited to, for Gastro-intestinal, cardio and/or ophthalmic applications, and being obtained via one or more optical instruments, such as, but not limited to, optical probes (e.g., common path probes), common path catheters, common path capsules and common path needles (e.g., a biopsy needle). Preferably, the OCT devices, systems methods and storage mediums include or involve a reference reflection or a reference plane that is at least one of: (i) disposed in the collimation field or path; and (ii) is perpendicular (or normal) or substantially perpendicular (or substantially normal) to light propagation. One or more embodiments may include beam shaping optics to properly image luminal or other hollow structures or objects.

20 Claims, 9 Drawing Sheets

(51) Int. Cl.
  *G01B 9/02056* (2022.01)
  *A61B 5/00* (2006.01)
  *G01B 9/02015* (2022.01)

(56) References Cited

U.S. PATENT DOCUMENTS

| | | | |
|---|---|---|---|
| 6,564,087 B1* | 5/2003 | Pitris | A61B 1/00172 600/478 |
| 7,426,036 B2 | 9/2008 | Feldchtein et al. | |
| 7,821,643 B2 | 10/2010 | Amazeen et al. | |
| 7,929,148 B2 | 4/2011 | Kemp | |
| 7,995,210 B2 | 8/2011 | Tearney et al. | |
| 8,049,873 B2 | 11/2011 | Hauger et al. | |
| 8,403,481 B2 | 3/2013 | Izatt et al. | |
| 8,820,931 B2 | 9/2014 | Walsh et al. | |
| 8,896,842 B2 | 11/2014 | Bower et al. | |
| 9,057,594 B2 | 6/2015 | Kang et al. | |
| 9,243,887 B2 | 1/2016 | Kang et al. | |
| 9,557,156 B2 | 1/2017 | Kankaria | |
| 10,568,520 B2* | 2/2020 | Patel | G02B 27/0911 |
| 2007/0236698 A1* | 10/2007 | Dogariu | G01N 21/4738 356/479 |
| 2008/0177138 A1* | 7/2008 | Courtney | A61B 5/0062 600/109 |
| 2008/0267562 A1* | 10/2008 | Wang | A61B 5/0062 385/31 |
| 2010/0053632 A1* | 3/2010 | Alphonse | G01B 9/02007 356/479 |
| 2010/0253949 A1* | 10/2010 | Adler | A61B 5/0068 356/479 |
| 2010/0305452 A1* | 12/2010 | Black | A61B 5/6852 600/476 |
| 2011/0261367 A1* | 10/2011 | Gmitro | A61B 5/0066 356/479 |
| 2012/0268578 A1* | 10/2012 | Vertikov | A61B 5/0066 348/65 |
| 2013/0271757 A1 | 10/2013 | Kang et al. | |
| 2013/0331709 A1* | 12/2013 | Le | G02B 6/32 600/478 |
| 2014/0066756 A1 | 3/2014 | Sinclair et al. | |
| 2014/0160482 A1 | 6/2014 | Tearney et al. | |
| 2015/0099984 A1* | 4/2015 | Kankaria | A61B 5/0066 600/478 |
| 2018/0045501 A1* | 2/2018 | Elmaanaoui | G01B 9/02015 |
| 2018/0256039 A1* | 9/2018 | Smith | A61B 5/6851 |

OTHER PUBLICATIONS

Xiaolu Li, et al., "Signal-to-noise ratio analysis of all-fiber common-path optical coherence tomography", Applied Optics, Optical Society of America, Washington, DC; US, vol. 47, No. 27, Sep. 20, 2008, pp. 4833-4840.

Xiaoyong Fu, et al., "Miniature forward-viewing common-path OCT probe for imaging the renal pelvis", Biomedical Optics Express, vol. 6, No. 4, Apr. 1, 2015, pp. 1164-1171.

Notification of Transmittal of the International Search Report and Written Opinion, and ISR/WO, for PCT/US2017/045721, dated Oct. 30, 2017.

Han, J.-H., et al., "Investigation of gold-coated bare fiber probe for in situ intra-vitreous coherence domain optical imaging and sensing", Applied Physics B, 2010, pp. 741-746, vol. 99, No. 4.

Liu, X., et al., "Optimization of an angled fiber probe for common-path optical coherence tomography", Opt. Lett., Aug. 1, 2013, pp. 2660-2662, vol. 38, No. 15.

Zhao, M., et al., "Sapphire ball lens-based fiber probe for common-path optical coherence tomography and its applications in corneal and retinal imaging". Opt. Lett., Dec. 1, 2012, pp. 4835-4837, vol. 37, No. 23.

Cimalla, P., et al., "Simultaneous dual-band optical coherence tomography in the spectral domain for high resolution in vivo imaging". Optics Express, 2009, pp. 19486-19500, vol. 17, No. 22.

Lorenser, D., Dual modality needle probe for combined fluorescence imaging and three-dimensional optical coherence tomography, Opt. Lett. 2013, pp. 266-268, vol. 38, No. 3.

* cited by examiner

Fig. 8
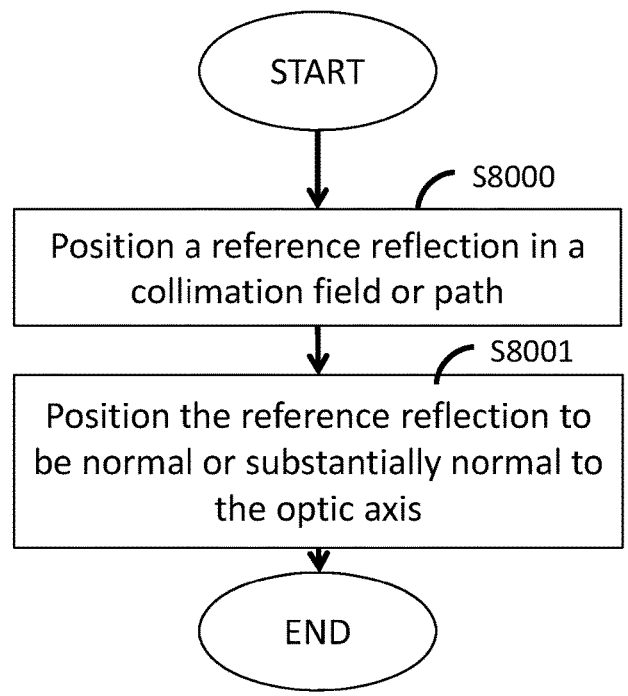
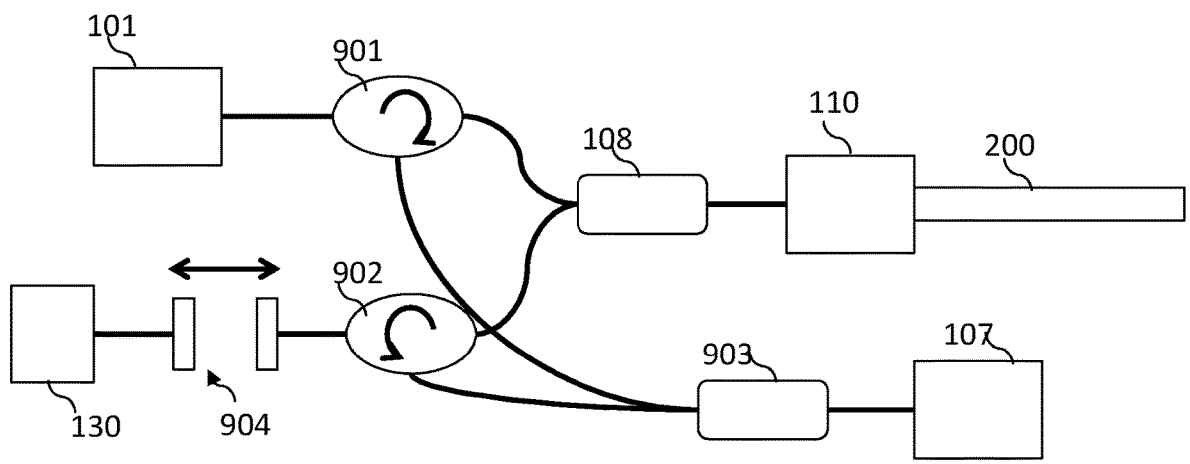
Fig. 9

COHERENCE RANGE IMAGING USING COMMON PATH INTERFERENCE

CROSS-REFERENCE TO RELATED APPLICATION(S)

This application claims priority to U.S. Provisional Application Ser. No. 62/374,324 field Aug. 12, 2016, the content of which is incorporated herein by reference in its entirety.

FIELD OF THE INVENTION

The present disclosure relates generally to the field of optical imaging and more particularly to optical coherence tomography (OCT) devices, systems, methods and storage mediums using a common path interference optical system, such as a common path interferometer, with a controlled reference signal and efficient geometric coupling. Examples of such applications include imaging, evaluating and diagnosing biological objects, such as, but not limited to, for gastro-intestinal, cardio and/or ophthalmic applications, and being obtained via one or more optical instruments, such as, but not limited to, one or more common path optical probes, one or more common path catheters, one or more common path endoscopes, one or more common path capsules, and one or more common path needles (e.g., a biopsy needle).

BACKGROUND OF THE INVENTION

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

A reference signal power level needs to be properly adjusted for a system signal-to-noise ratio (SNR) to be maximized. However, if the reference coupling efficiency is low or if it is not possible to properly adjust to a desired reference signal power level, then it may be difficult to maximize SNR.

Using certain types of materials is one way to try to set or determine a specific reference signal value. However, such use of certain materials can lead to a discreet set of values only because of the possibility of having a difference(s) between an index of refraction for selected materials.

Using coatings may help control a reference power over a broad range, but only if the coupling efficiency is high and deterministic, which is especially true for common path interferometry with an adjustment section where the adjustment section increases loss in a reference path and/or where light throughput in the interferometer is low. As such, when coupling efficiency is less than ideal in devices using an adjustment section, even more light is lost. However, reference light has not been efficiently coupled back to a fiber, and, therefore, the reference light cannot properly be used to image luminal or other hollow structures. The difficulty in imaging when the reference signal is too low or sometimes too high applies generally to all sample types and structures. When the signal is too high, other sources of noise start to overtake the SNR.

The aforementioned structures can lead to one or more of path length mismatches, dispersion mismatches and/or polarization mismatches while making one or more measurements.

Additionally, depending on the type of OCT used (e.g., Spectral Domain OCT ("SD-OCT"), Swept-source OCT ("SS-OCT"), Time-Domain OCT ("TD-OCT"), etc.), one or more settings (e.g., reference power, sensitivity, required reference reflection, etc.) of the OCT device or system may need to be adjusted because such settings may vary based on the type of OCT used. For example, a required reference reflection for an SD-OCT device or system may vary greatly from a required reference reflection for an SS-OCT device or system, and both can vary based on noise characteristics of the system, especially a light source.

Accordingly, it would be desirable to provide at least one OCT technique and/or device for use in at least one optical device, assembly or system to achieve efficient coupling and a controlled reference signal, especially in a way that reduces or minimizes cost of manufacture and maintenance.

SUMMARY OF THE INVENTION

Accordingly, it is a broad object of the present disclosure to provide OCT devices, systems, methods and storage mediums using a common path interference optical system, such as a common path interferometer (e.g., SD-OCT, SS-OCT, etc.), with a controlled and efficient reference signal or reference reflection, and with efficient geometric coupling of said reflection.

In accordance with one or more aspects of the present disclosure, at least one embodiment of a common path optical coherence tomography system includes: a common path interference optical system that operates to: (i) receive and divide light from a light source into a first light with which an object or sample is to be irradiated and which travels along a sample arm of the common path interference optical system and a second reference light, (ii) send the second reference light along a reference arm of the common path interference optical system for reflection off of a reference reflection of the common path interference optical system, and (iii) generate interference light by causing reflected or scattered light of the first light with which the object or sample has been irradiated and the reflected second reference light to combine or recombine, and/or to interfere, with each other, the interference light generating one or more interference patterns, wherein the reference arm overlaps with at least a portion of the sample arm; and at least one detector that operates to continuously acquire the interference light and/or the one or more interference patterns to measure the interference or the one or more interference patterns between the combined or recombined light.

In one or more embodiments of the system, (i) the position of the reference reflection may be configured to maximize coupling efficiency of a return signal of light passing therethrough; and/or (ii) the reference reflection may be positioned in a path of the light such that the reference reflection is perpendicular or substantially perpendicular to an optic axis of the light. The reference reflection may include an optical coating to improve or optimize a reflection value for the reference reflection or is additionally angled to improve or optimize the second reference light or a signal therefor.

In one or more embodiments, the common path interference optical system may include a probe having: a fiber attached to a collimator, a no core fiber (NCF) or large core multimode fiber and a lens having the reference reflection disposed thereon or therein, and wherein at least one of: (i) the fiber attached to the collimator operates as a signal carrying optical fiber; and (ii) the fiber attached to the collimator comprises: a single mode fiber (SMF), a double clad fiber (DCF), or a multimode fiber. The lens may be spaced away from the fiber and the NCF or large core multimode fiber. The lens may be angled or tilted with respect to the fiber and the NCF or large core multimode fiber, or the lens may be flat or not tilted with respect to the fiber and the NCF or large core multimode fiber such that the lens is parallel or substantially parallel to an axis extending through or along a length of the probe or the common path optical coherence tomography system. The lens may be at least one of: an off-axis lens and a lens that forces the light to be angled. In one or more embodiments, at least one of the following may occur: (i) the probe further includes a spacer positioned between the fiber and the collimator, the spacer operating to further broaden the light beam or beams; (ii) the spacer comprises at least one of: fused silica, a large core multimode fiber, fluid, an index matching fluid, and an epoxy with a specific index of refraction; (iii) the probe is positioned in a sheath; (iv) the collimator is a collimating gradient index (GRIN) lens or fiber that is fusion spliced to the fiber; (v) the NCF or large core multimode fiber is fusion spliced to the collimator comprising a GRIN lens or fiber; (vi) the NCF or large core multimode fiber is polished at an angle that meets a total internal reflection (TIR) condition and is larger than 45 degrees or larger than about 45 degrees so as to reduce or minimize undesired reflection(s) from a side surface of the NCF or large core multimode fiber; and (vii) the lens includes an astigmatism to correct or compensate for use of the sheath.

In one or more additional embodiments, the common path interference optical system may include a probe having: a fiber attached to a collimator, a no core fiber (NCF) or large core multimode fiber and a lens, where the reference reflection is located or situated in a second polished lateral surface of the NCF or large core multimode fiber, and wherein at least one of: (i) the fiber attached to the collimator operates as a signal carrying optical fiber; and (ii) the fiber attached to the collimator comprises: a single mode fiber (SMF), a double clad fiber (DCF), or a multimode fiber. At least one of the following may exist: (i) the lens includes a curved surface that operates to interact with the light passing through the lens and that reduces one or more aberrations; and (ii) the curved surface is disposed on a first side of the lens such that the curved surface is positioned between the lens and the NCF or large core multimode fiber or the curved surface is disposed on a second side of the lens such that the curved surface is positioned in between the lens and the object or sample. The reference reflection may be disposed in a flat portion of a lateral surface of the NCF or large core multimode fiber, or the reference reflection may be disposed in an angled or tilted portion of the lateral surface of the NCF or large core multimode fiber. At least one of the following may exist: (i) the lens is spaced away from the fiber and the NCF or large core multimode fiber; (ii) the lens is angled or tilted with respect to the fiber and the NCF or large core multimode fiber, or the lens is flat or not tilted with respect to the fiber and the NCF or large core multimode fiber; (iii) the collimator is a collimating gradient index (GRIN) lens or fiber that is fusion spliced to the fiber; (iv) the NCF or large core multimode fiber is fusion spliced to the collimator comprising a GRIN lens or fiber; and (v) the NCF or large core multimode fiber is polished at an angle that meets a total internal reflection (TIR) condition and is larger than 45 degrees or larger than about 45 degrees so as to reduce or minimize undesired reflection(s) from a side surface of the NCF or large core multimode fiber.

The common path interference optical system may include a probe having: (i) a fiber operating to receive, and pass therethrough, the first light and the second reference light and the fiber including the reference reflection positioned at an end of the fiber; and (ii) a reflector operating to reflect the first light passing through the fiber and the reference reflection of the fiber along the sample arm towards the object or sample, and to reflect the light having illuminated the object or sample back into the fiber towards the at least one detector, and wherein at least one of: (i) the fiber operates as a signal carrying optical fiber; and (ii) the fiber comprises: a single mode fiber (SMF), a double clad fiber (DCF), or a multimode fiber. At least one of the following may exist: (i) the probe further includes a lens spaced away from the reflector, the lens operating to receive the light reflecting off of the reflector and pass the light therethrough along the sample arm towards the object or sample, and then, after the light illuminates the object or sample, to pass the light through the lens back towards the reflector and into the fiber towards the at least one detector; (ii) the lens is tilted or angled with respect to the fiber, or the lens is flat or not tilted with respect to the fiber; (iii) the reflector is a dielectric or metal mirror or reflector; (iv) the reflector is flat or curved for astigmatism correction; and (v) the reflector is positioned on a reflector substrate located in the probe, the reflector substrate including at least one of: glass, injection molded plastic, epoxy and metal.

The common path interference optical system may include a probe having: (i) a fiber operating to receive, and pass therethrough, the first light and the second reference light and the fiber including the reference reflection positioned at an end of the fiber; and (ii) a no core fiber (NCF) or prism or large core multimode fiber positioned on the other side of the reference reflection such that the reference reflection is located between the fiber and the NCF or prism or large core multimode fiber, wherein the NCF or prism or large core multimode fiber operates to reflect the first light passing through the fiber and the reference reflection of the fiber along the sample arm towards the object or sample, and to reflect the light having illuminated the object or sample back into the fiber towards the at least one detector, and wherein at least one of: (i) the fiber operates as a signal carrying optical fiber; and (ii) the fiber comprises: a single mode fiber (SMF), a double clad fiber (DCF), or a multimode fiber. At least one of the following may exist: (i) the probe further includes a lens spaced away from the NCF or prism or large core multimode fiber, the lens operating to receive the light reflecting off of the NCF or prism or large core multimode fiber and pass the light therethrough along the sample arm towards the object or sample, and then, after the light illuminates the object or sample, to pass the light through the lens back towards the NCF or prism or large core multimode fiber and into the fiber towards the at least one detector; and (ii) the lens is tilted or angled with respect to the fiber, or the lens is flat or not tilted with respect to the fiber.

In one or more embodiments, the common path interference optical system may further include a collimator that operates to collimate the light traveling therethrough. The reference reflection may be positioned in a collimation field or path of the collimated light.

In at least one embodiment, at least one of following may exist: (i) the reference reflection comprises an anti-reflective (AR) coating, a high reflection (HR) coating, or a partial mirror; and (ii) the reference reflection allows for an improved or maximized signal-to-noise ratio (SNR).

A common path optical coherence tomography system may further include at least one of: (i) the light source that operates to produce the light; and (ii) a guide or waveguide for transmitting the light from the light source. A common path optical coherence tomography system may further include a deflecting section that operates to deflect the light from the light source to the common path interference optical system, and then send light received from the common path interference optical system towards the at least one detector. The deflecting section may include at least one of: one or more common path interferometers, a circulator, a beam splitter, an isolator, a coupler, a fusion fiber coupler, a partially severed mirror with holes therein, and a partially severed mirror with a tap. The reference arm and the sample arm may overlap or share a common path between the deflecting section and the reference reflection. The reference arm may extend between the deflecting section and the reference reflection. The sample arm may extend between the deflecting section and the object or sample and the sample arm may extend via or through the reference reflection. In one or more embodiments, the reference arm may be spaced away from the object or sample, and the sample arm may be disposed or may extend between a portion of the reference arm and the object or sample.

A common path optical coherence tomography system may further include an adjustment section that operates to control one or more relative optical characteristics between the first light having illuminated the object or sample and the reflected second light, wherein the deflecting section further operates to pass the light from the probe to the adjustment section and towards the at least one detector.

In one or more embodiments, a common path optical coherence tomography system may further include a catheter including a sheath, a coil, a protector and an optical probe, wherein: (i) the coil delivers torque from a proximal end to a distal end thereof; (ii) the coil is fixed with/to the optical probe so that a distal tip of the optical probe also spins to see an omnidirectional view of the object or sample being evaluated; (iii) the catheter is disposed at least in the sample arm; (iv) the optical probe is simultaneously translated longitudinally during the rotational spin resulting in a helical scanning pattern to acquire three-dimensional data of the object or sample; and (v) the translation is performed by pulling a tip of the optical probe back towards the proximal end.

A common path optical coherence tomography system may further include at least one processor that operates to process a signal from the at least one detector to acquire information of the object or sample.

In accordance with another aspect of the present disclosure, a method for performing common path optical coherence tomography ("OCT") using a common path OCT device or system having a common path interference optical system that operates to generate interference light and one or more interference patterns from a light that has been split into a first light with which an object or sample has been irradiated and a second reference light and having at least one detector, may include: positioning a reference reflection of the common path interference optical system such that at least one of: (i) the reference reflection is perpendicular, or substantially perpendicular, to an optic axis of the common path interference optical system or the common path OCT device or system; and (ii) the position of the reference reflection is configured to maximize coupling efficiency of a return signal of light passing therethrough. The method may further include at least one of: (i) sending the second reference light along a reference arm of the common path interference optical system for reflection off of the reference reflection of the common path interference optical system; (ii) receiving the light from a light source; (iii) splitting the light from the light source into the first light and the second reference light to generate the interference light; (iv) positioning the reference reflection in a collimation field or path of the common path interference optical system; and (v) acquiring, via the at least one detector, the interference light and/or the one or more interference patterns to measure the interference or the one or more interference patterns. The reference arm may overlap with at least a portion of a sample arm of the common path interference optical system, and the first light may travel along the sample arm of the common path interference optical system.

In accordance with a further aspect of the present disclosure, a computer-readable storage medium may be used for storing a program that operates to cause one or more processors to perform a method for performing common path optical coherence tomography ("OCT") using a common path OCT device or system having a common path interference optical system that operates to generate interference light and one or more interference patterns from a light that has been split into a first light with which an object or sample has been irradiated and a second reference light and having at least one detector, the method comprising: positioning a reference reflection of the common path interference optical system such that at least one of: (i) the reference reflection is perpendicular, or substantially perpendicular, to an optic axis of the common path interference optical system or the common path OCT device or system; and (ii) the position of the reference reflection is configured to maximize coupling efficiency of a return signal of light passing therethrough.

In accordance with at least one aspect of the present disclosure, one or more common path OCT techniques are provided where a reference plane or a reflection surface resides in the collimation field or path and is perpendicular (or normal), or substantially perpendicular (or substantially normal—"substantially" encompassing all workable ranges for performing OCT), to light propagation or an optical axis. In one or more embodiments, reference signal power may be chosen over a wide range of values even when there is a lot of loss in the device or system. Indeed, a reference reflection value may be precisely dialed over a broad range of values. In one or more embodiments, the effect of undesired reflections from a probe are reduced or minimized because such undesired reflections are not in the collimated field and/or are not normal to the optical axis. Additionally, in one or more embodiments, a number of optical components inside a probe housing, or of the common path OCT system or apparatus, may be reduced or minimized.

In accordance with at least another aspect of the present disclosure, the common path OCT technique(s) discussed herein may be employed with beam shaping optics for imaging luminal, intraluminal or other hollow structures. For example, in at least one embodiment, an additional lens (e.g., an anamorphic lens, a gradient index (GRIN) lens or fiber, a Ball lens, etc.) may be placed in the path of the light to provide a desired beam profile and correct for astigmatism introduced by a protective sheet or window element. One or more embodiments provide the ability to efficiently couple a reference reflection and shape a light beam for imaging of the aforementioned structures.

In accordance with at least another aspect of the present disclosure, the common path OCT technique(s) discussed herein may be employed to reduce the cost of at least one of manufacture and maintenance of OCT devices, systems and storage mediums by reducing or minimizing a number of optical components in an interference optical system, such as an interferometer. A common path probe may include a reference arm and a sample arm, and may include an optical fiber and other optical materials. In one or more embodiments, the reference arm and the sample arm may be included in a probe housing to prevent path length mismatches, dispersion mismatches and/or polarization mismatches while making one or more measurements.

In accordance with at least a further aspect of the present disclosure, the common path OCT technique(s) discussed herein may be used with or without an adjustment section in or used with an interference optical system, such as an interferometer.

The common path OCT technique(s) may be used in at least one device, such as, but not limited to, a Fourier spectrometer, one or more common path optical probes, one or more common path catheters, one or more common path endoscopes, one or more common path capsules, and one or more common path needles (e.g., a biopsy needle), to create an optical spectrum from a light/radiation beam and/or an electrical signal created from the light/radiation beam.

In accordance with yet a further aspect of the present disclosure, regular probes, as well as common path probe(s), are provided for OCT (e.g., SS-OCT, SD-OCT, etc.). One or more differences between regular probes and common path probes may relate to a specific coating on the single reference surface.

According to other aspects of the present disclosure, one or more additional devices, one or more systems, one or more methods and one or more storage mediums using common path OCT are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 8 is a flow diagram showing a method of performing common path OCT in accordance with one or more aspects of the present disclosure;

FIG. 9 shows a schematic diagram of an embodiment of an interferometer using a common path probe in accordance with one or more aspects of the present disclosure.

DETAILED DESCRIPTION OF THE PRESENT INVENTION

One or more devices, optical systems, methods and storage mediums for performing coherence range imaging using a common path OCT technique are disclosed herein. In accordance with at least one aspect of the present disclosure, one or more devices, optical systems, methods and storage mediums discussed herein use a common path OCT technique with a controlled reference signal and efficient geometric coupling.

Figure 1:
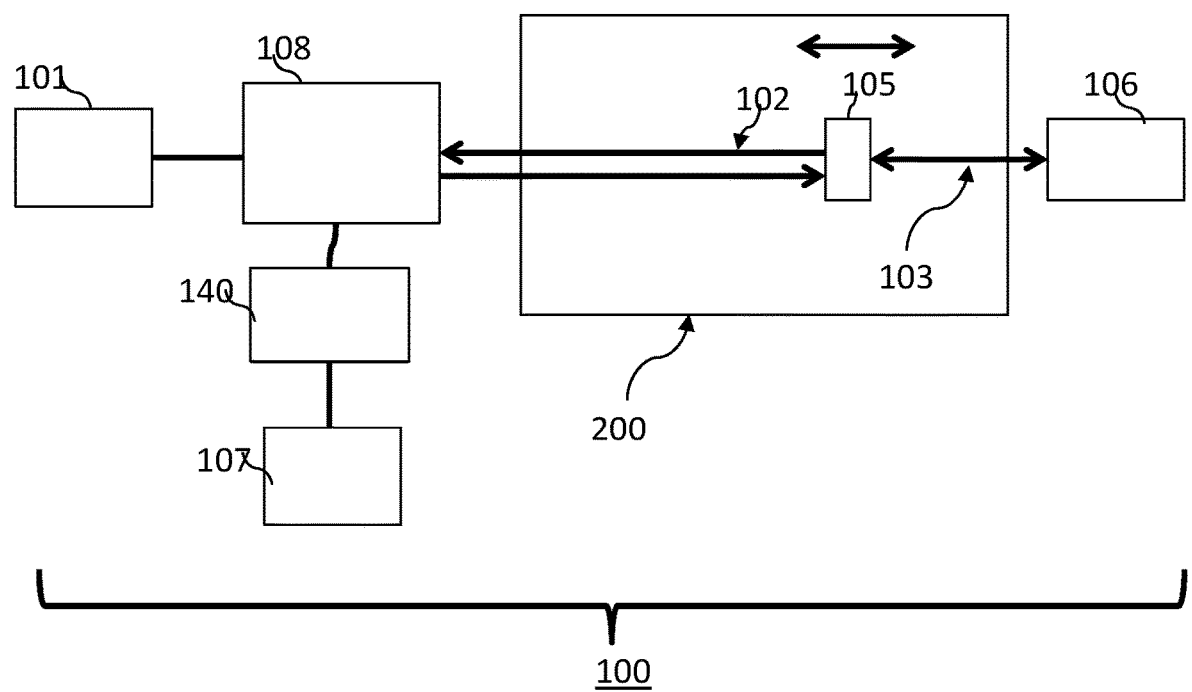
FIG. 1 is a diagram showing an embodiment of a system which can utilize a common path OCT technique with optical probe applications in accordance with one or more aspects of the present disclosure.

Turning now to the details of the figures, FIG. 1 shows an embodiment of an interference optical system 100 (as referred to herein as "system 100" or "the system 100") which operates to utilize a common path OCT technique with optical probe applications in accordance with one or more aspects of the present disclosure. The system 100 comprises a light source 101, a reference arm 102, a sample arm 103, a deflected section 108 (e.g., a collimating lens or fiber; the deflected section 108 is also referred to herein as a deflecting section 105), a reference mirror (also referred to herein as a "reference reflector", "reference reflection", "partially reflecting mirror" and a "partial reflector") 105 (which may be included in a common path probe or probe housing 200 as shown in the embodiment of FIG. 1) and at least one detector 107. The system 100 may interact with a sample, specimen or object 106, via the sample arm 103 (as schematically shown in FIG. 1), and the system may 100 may include an adjustment section 140. Preferably, the reference arm 102 and the sample arm 103 share a common path between the deflected section 108 and the reference reflection 105. The reference arm 102 extends between the deflected section 108 and the reference reflection 105. The sample arm 103 extends between the deflected section 108 and the sample 106, via or through the reference reflection 105.

Preferably, the deflected section 108 operates to deflect the light from the light source 101 to the common path probe or probe housing 200, and then send light received from the common path probe or probe housing 200 towards the at least one detector 107. In one or more embodiments, the deflected section 108 of the system 100 may include or may comprise one or more common path interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the common path interferometer or the common path optical interference system may include one or more components of the system 100, such as, but not limited to, one or more of the light source 101, the reference arm 102, the sample arm 103, the deflected section 108 and/or the reference reflection 105.

In one or more embodiments, the reference reflector or reference reflection 105 is preferably disposed in the system 100 such that the reference reflector or reference reflection 105 at least one of: (i) resides in the collimation field or path (e.g., in a partially or wholly collimated field or path) and (ii) is normal (or substantially normal) or perpendicular (or substantially perpendicular) to an optic axis (e.g., an axis along which there is, or is some degree of, rotational symmetry in an optical system (such as, but not limited to, the system 100, a probe 200, 200a, 200', 200a', 200", 200a", 200''', 200a''', 200'''' (see e.g., FIGS. 2A-6), etc.); an axis that defines a path along which light from the light source 101 spreads through an optical system (such as, but not limited to, the system 100, one of the probes 200, 200a, 200', 200a', 200", 200a", 200''', 200a''', 200'''' etc.); an axis that defines a path along which there is, or is some degree of, rotational symmetry in an optical system (such as, but not limited to, the system 100, one of the probes 200, 200a, 200', 200a', 200", 200a", 200''', 200a''', 200'''', etc.); an axis along a core of an optical fiber (see e.g., fiber 201 as shown in any of FIGS. 2A-6); an optical axis along a center of a core of an optical fiber (see e.g., fiber 201 as shown in any of FIGS. 2A-6); an axis defining a path passing through a collimation field and along which there is, or is some degree of, rotational symmetry (see e.g., FIGS. 2A-6 which are discussed further below); etc.). In one or more embodiments, the reference arm 102 overlaps with the sample arm 103, and the reference arm 102 is spaced away from the sample 106. In one or more embodiments, the reference reflection 105 may include an optical coating to optimize a desired reflection value for the reference reflection 105. In one or more embodiments, changing an the angle of the reference reflector or reference reflection 105 with respect to the optic axis may be used to improve or optimize the reference signal, including in situations where an optical coating or other material choice may not be at nominal design value(s). For example, when intentionally further tilting the angle of the reference reflector or reference reflection 105, preferably the further angle tilt is at least one of: 1-3 degrees, 0-2 degrees, about 1 degree to about 3 degrees, about 0 degrees to about 2 degrees.

Figure 2A:
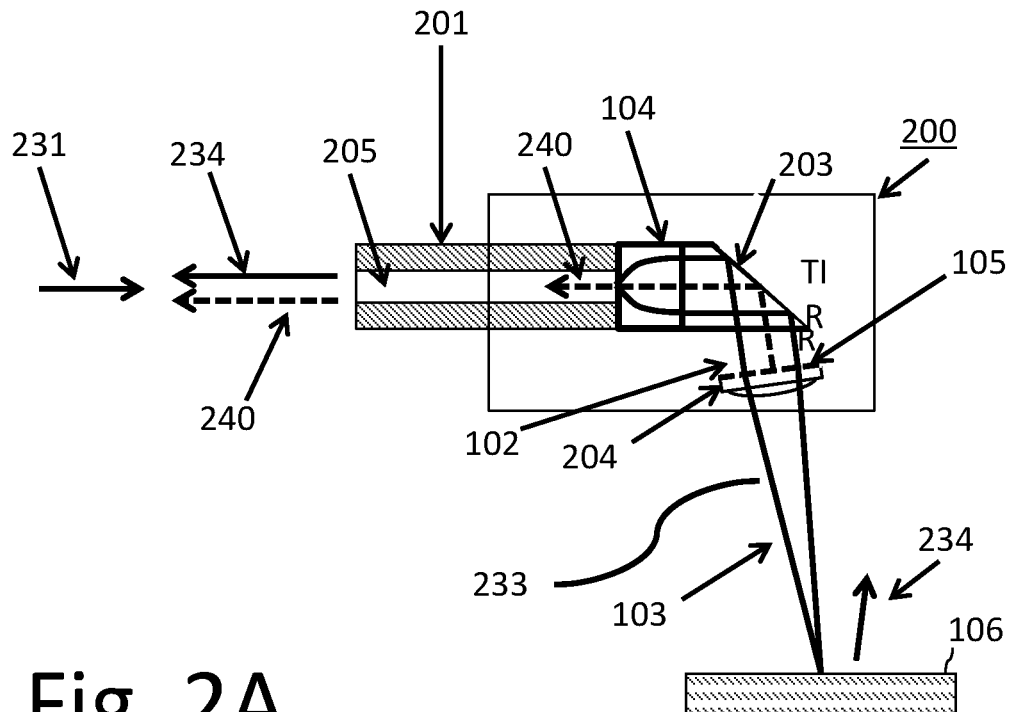
FIG. 2A is a diagram showing an embodiment of a common path probe having a reference reflection disposed on a tilted lens for use with at least one OCT device or system in accordance with one or more aspects of the present disclosure.
Figure 7:
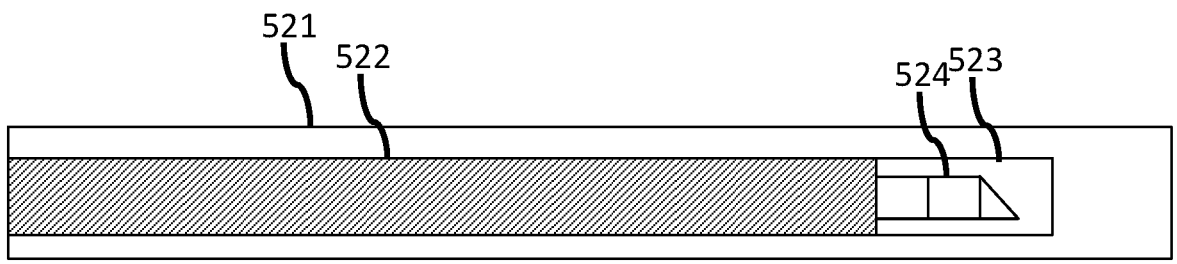
FIG. 7 is a diagram of an embodiment of a catheter that may used with at least one embodiment of a common path OCT technique with optical probe applications in accordance with one or more aspects of the present disclosure.

In one or more embodiments, the system 100 may include, or be used with, a probe 200 having a fiber 201 attached to a collimator 104 (e.g., a collimating lens or fiber), a no core fiber (NCF) or large core multimode fiber 203 (which may be glass, plastic or any other alternative to a fiber with a core in one or more embodiments, which may be a flat or cylindrical prism, which may be a surface having a reflection that is polished flat, etc.), and a lens 204 (may be any lens, such as, but not limited to, an anamorphic lens, and may or may not be off-axis, may or may not be angled, etc.) having the reference reflection 105 disposed thereon or therein as shown in at least FIG. 2A. The light from the light source 101 is sent through the system 100 (e.g., via the deflected section 108) to the collimator 104, for example, via the fiber 201. In other words, the fiber 201 operates as a signal carrying optical fiber, such as, but not limited to, a single mode fiber (SMF), a double clad fiber (DCF), a multimode fiber or other type of signal carrying fiber. In the preferred embodiment, the collimator 104 may be a mostly collimating gradient index (GRIN) lens or fiber that is fusion spliced to the signal carrying optical fiber 201. In one or more embodiments, the no core fiber (NCF) or large core multimode fiber 203 is then fusion spliced to the GRIN lens or fiber (e.g., an embodiment of the collimator 104). Preferably, the NCF 203 is polished at an angle that meets a total internal reflection (TIR) condition and is larger than 45 degrees or larger than about 45 degrees so as to minimize undesired reflection(s) from a side surface of the NCF 203 (and a catheter sheath, which may be employed with the NCF 203 in one or more embodiments of the system 100). In one or more embodiments using a catheter sheath (see e.g., the sheath 521 as shown in FIG. 7 and as discussed below), the catheter sheath may affect the light detrimentally such that an astigmatism may be introduced into the lens 204 to correct or compensate for the use of the sheath. In one or more embodiments, one or more angles other than larger than 45 degrees or larger than about 45 degrees may be used (e.g., 30 degrees, 35 degrees, 40 degrees, 50 degrees, 60 degrees, or any other angle that allows the device to function as described herein) while achieving the effect of reducing or avoiding reflections from a sheath, a side surface of the NCF 203, etc. For example, in one or more embodiments, a connection component (or interface module), such as a rotary junction, may be used to connect one or more components, such as one or more components of a probe (e.g., the probe 200 or one or more components thereof (e.g., the reference reflection 105)), a needle, a capsule, a patient interface unit (e.g., interface unit 110), etc., to one or more other components, such as, an optical component, a light source (e.g., the light source 101), a deflection section (e.g., the deflection or deflected section 108), etc. For example, when the connection member or interface module is a rotary junction, the rotary junction may be at least one of: a contact rotary junction, a lenseless rotary junction, a lens-based rotary junction, or other rotary junction known to those skilled in the art.

Preferably, the lens 204 including the reference reflection 105 is placed in the path of the light to provide a desired beam profile. Such positioning of the lens 204 having the reference reflection 105 also corrects for astigmatism from a catheter sheath when the catheter sheath is used with the system 100 in one or more embodiments. The first surface of the lens 204, used as the reference reflection 105, is mostly flat and may be normal, substantially normal (e.g., ±a few degrees from normal, about 87 degrees to about 93 degrees, about 88 degrees to about 92 degrees, about 89 degrees to about 91 degrees, any angle or range of angles that would improve coupling efficiency, etc.) to the optic axis to maximize coupling efficiency of the return signal to a core 205 of the fiber 201. The angle of the reference reflection 105 may be any other angle or range of angles that improves coupling efficiency even if not normal or substantially normal to the optic axis. The reference reflection 105 can be optimized through choice of material and/or optical coating (e.g., an anti-reflective (AR) coating, a high reflection (HR) coating, a partial mirror, etc.). This type of setup allows for an improved or a maximized signal-to-noise ratio (SNR) (especially when coupling efficiency is improved or high) and is also an efficient setup when used for coherence range imaging using a common path interferometer with an adjustment section. In one or more embodiments, lens tilting (see e.g., FIGS. 2A-3B and FIGS. 5B-6) of the lens 204 may be used as an additional way of adjusting coupling efficiency. The light 231 goes through the optical fiber 201, and a part of the light (a reference beam) 240 is reflected at the reference reflection 105 and sent back through the fiber 201. The rest of the light 233 illuminates the sample 106, and the reflected and/or scattered light (sample beam) 234 from the sample 106 is sent through the lens 204 and is delivered to the fiber 201 via the NCF and the collimator 104. Preferably, the sample beam 234 and the reference beam 240 are coupled, combined or recombined and go back to the deflection section 108, which thereafter sends the recombined beam towards the at least one detector 107.

The output of the one or more components of the system 100 (e.g., one or more of the probe 200, the deflected section 108, the adjustment section 140, etc.) is acquired with the at least one detector 107, e.g., such as, but not limited to, photodiodes or multi-array cameras. The at least one detector 107 measures the interference or interference patterns between the two radiation or light beams (e.g., the reference beam 240 and the sample beam 234 as shown in FIG. 2A) that are coupled, combined or recombined. In one or more embodiments, the reference and sample beams have traveled different optical path lengths such that a fringe effect is created and is measurable by the at least one detector 107. Electrical analog signals obtained from the output of the system 100 and/or the interferometer thereof are converted to digital signals to be analyzed with a computer, such as, but not limited to, the computer 1200 (shown in FIG. 10 discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Figure 2B:
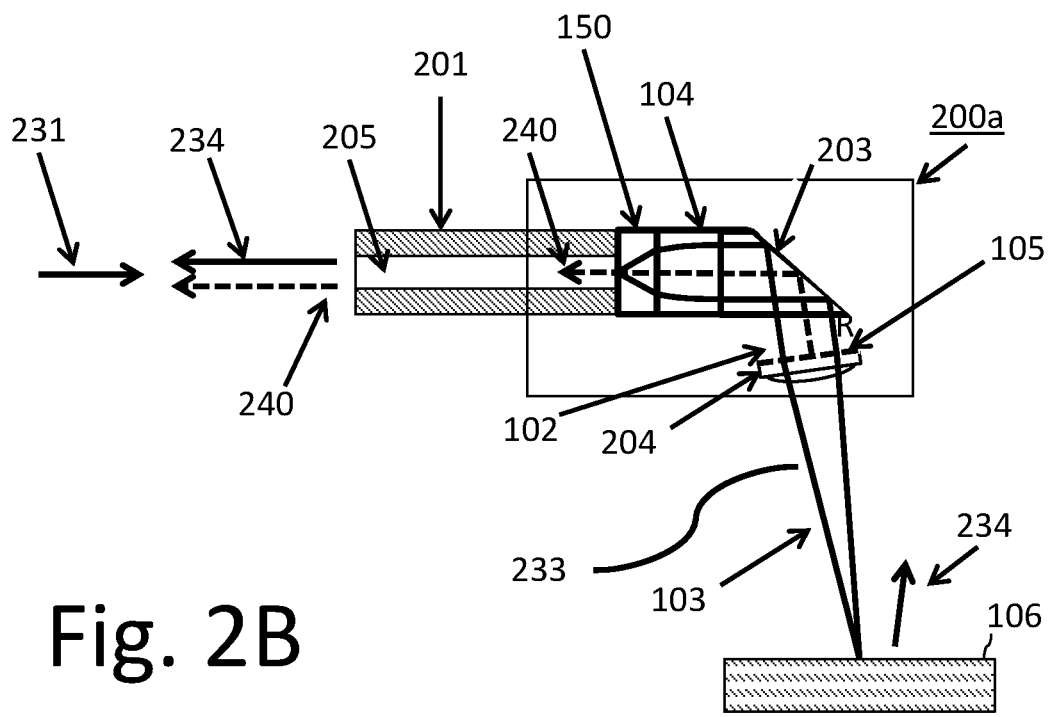
FIG. 2B is a diagram showing an alternative embodiment of the common path probe of FIG. 2A including a spacer for use with at least one OCT device or system in accordance with one or more aspects of the present disclosure.

Additionally or alternatively, as best seen in FIG. 2B, the probe 200 may further include a spacer 150 (when the probe 200 includes the spacer 150, the probe 200 may be referred to as probe 200a to indicate such a modification from the probe 200 shown in FIG. 2A). In one or more embodiments, the spacer 150 may be useful to include, and may comprise one or more of: fused silica, a large core multimode fiber, fluid (index matching fluid) or epoxy with a specific index of refraction or the like. A spacer 150 may further broaden the light beam or beams before the beam or beams go to the collimator 104 to end up as a larger beam or beams. The beam(s) may be focused more efficiently when the beam(s) have a larger diameter.

Figure 2C:
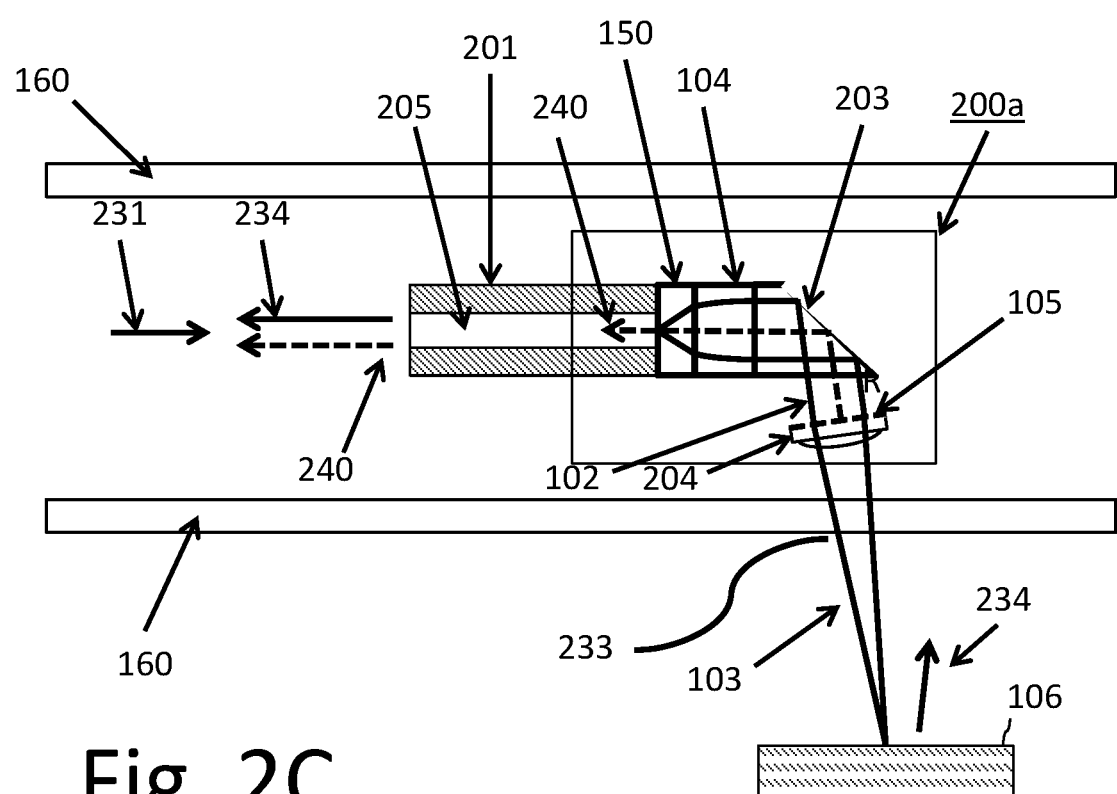
FIG. 2C is a diagram showing the embodiment of the common path probe of FIG. 2B being positioned or located in a sheath for use with at least one OCT device or system in accordance with one or more aspects of the present disclosure.

As shown in FIG. 2C, the probe 200a may be disposed or positioned in a sheath 160. The sheath 160 may be transparent or semitransparent, may be extruded, and may be single or multilayer. In one or more embodiments, the sheath 160 may be employed with the probe 200a in any application, such as, but not limited to, a common path OCT needle, a common path OCT capsule, etc. The probe 200a is used with the sheath 160 for illustrative purposes, and any probe 200, 200', 200a', 200'', 200a'', 200''', 200a''', 200'''', etc. discussed herein may be used with the sheath 160. Those skilled in the art will appreciate that the sheath 160 may be similar in one or more respects or may be used interchangeably in one or more embodiments with the sheath 521 discussed herein.

Figure 3A:
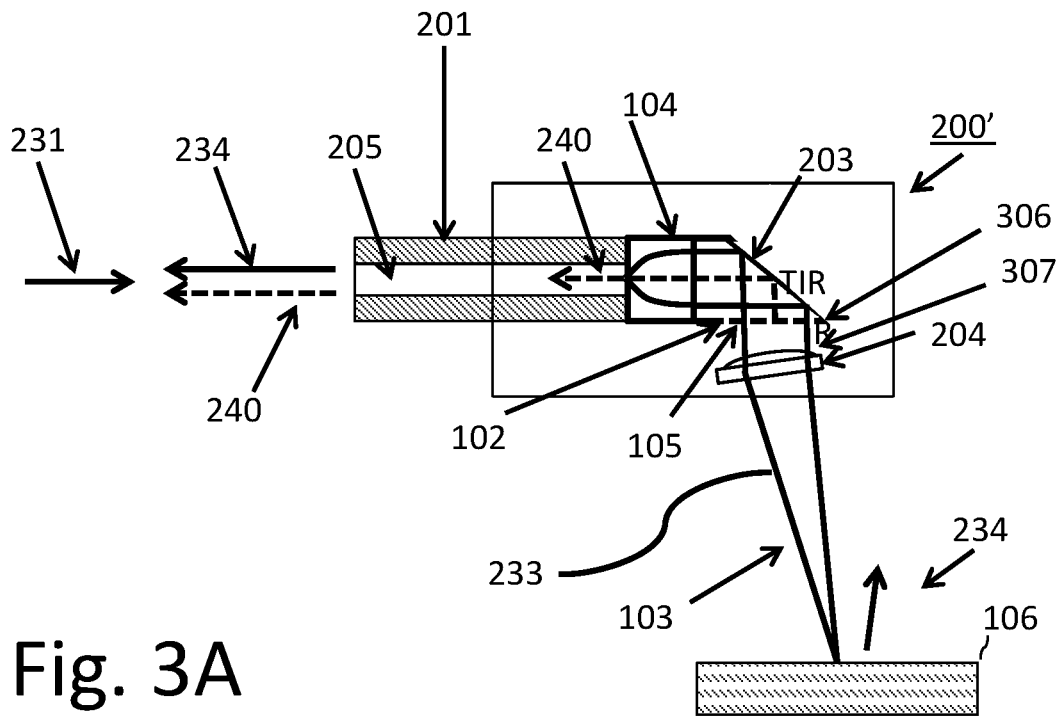
FIG. 3A is a diagram showing another embodiment of a common path probe having a reference reflection disposed in or on a second polished lateral surface of a no core fiber and having a tilted lens for use with at least one OCT device or system in accordance with one or more aspects of the present disclosure.

In accordance with at least another aspect of the present disclosure, one or more alternative embodiments of the system 100 may include a probe 200' having the reference reflection 105 being disposed or situated in a second polished lateral surface 306 of the NCF 203 (see FIG. 3A). The light interacts with the curved surface 307 of the lens 204 first to reduce aberrations and the lens 204 can be tilted and/or off axis to angle the beam propagation direction. As shown in FIG. 3A, the curved surface 307 is disposed on the lens 204 to be positioned in between the lens 204 and the NCF 203 (in contrast with the embodiment shown in FIG. 2A where a curved surface of the lens 204 is disposed on the opposite side of the lens 204 between the lens 204 and the sample 106). The embodiment shown in FIG. 3A is the same as the embodiment shown in FIG. 2A except for the reference reflection being situated in the second polished lateral surface 306 of the NCF 203 and except for the curved surface 307 being disposed on the lens 204 on the opposite side of the lens 204 (i.e., on the side opposite to the side of the lens 204 having a curved surface as shown in FIG. 2A). In one or more embodiments, the lens 204 is an off-axis, tilted lens, and the lens 204 forces the light to be angled.

Figure 3B:
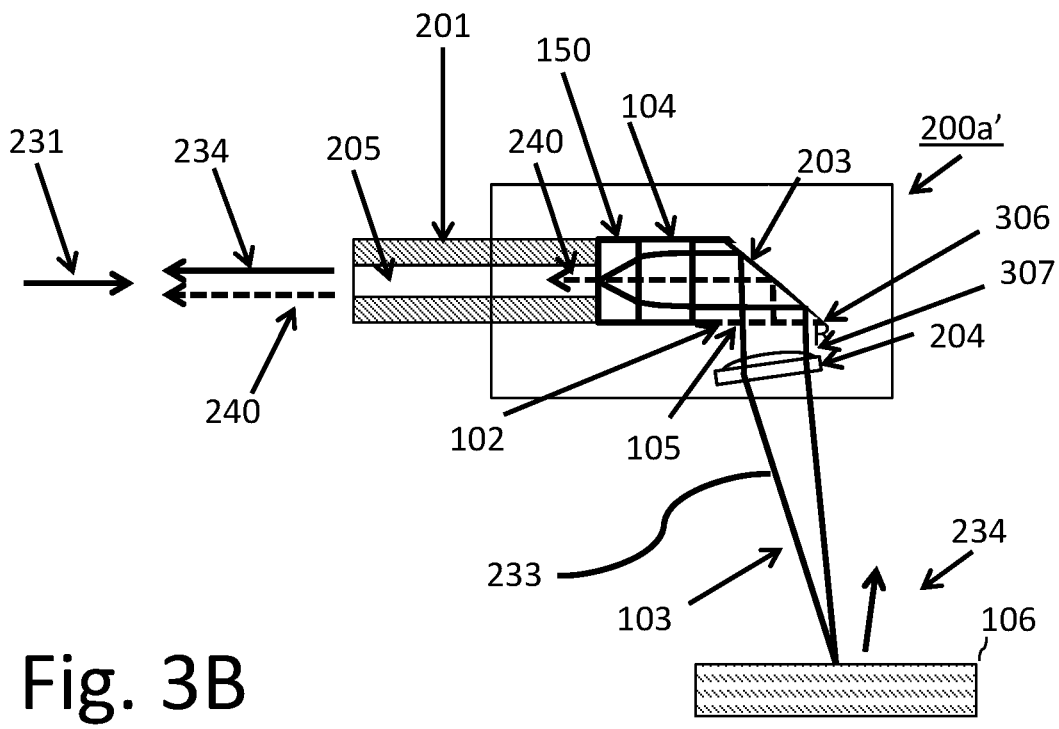
FIG. 3B is a diagram showing an alternative embodiment of the common path probe of FIG. 3A including a spacer for use with at least one OCT device or system in accordance with one or more aspects of the present disclosure.

Additionally or alternatively, as best seen in FIG. 3B, the probe 200' may further include a spacer 150 (when the probe 200' includes the spacer 150, the probe 200' may be referred to as probe 200a' to indicate such a modification from the probe 200' shown in FIG. 3A). In one or more embodiments, the spacer 150 may be useful to include, and may comprise one or more of: fused silica, a large core multimode fiber, fluid (index matching fluid) or epoxy with a specific index of refraction or the like.

Figure 4A:
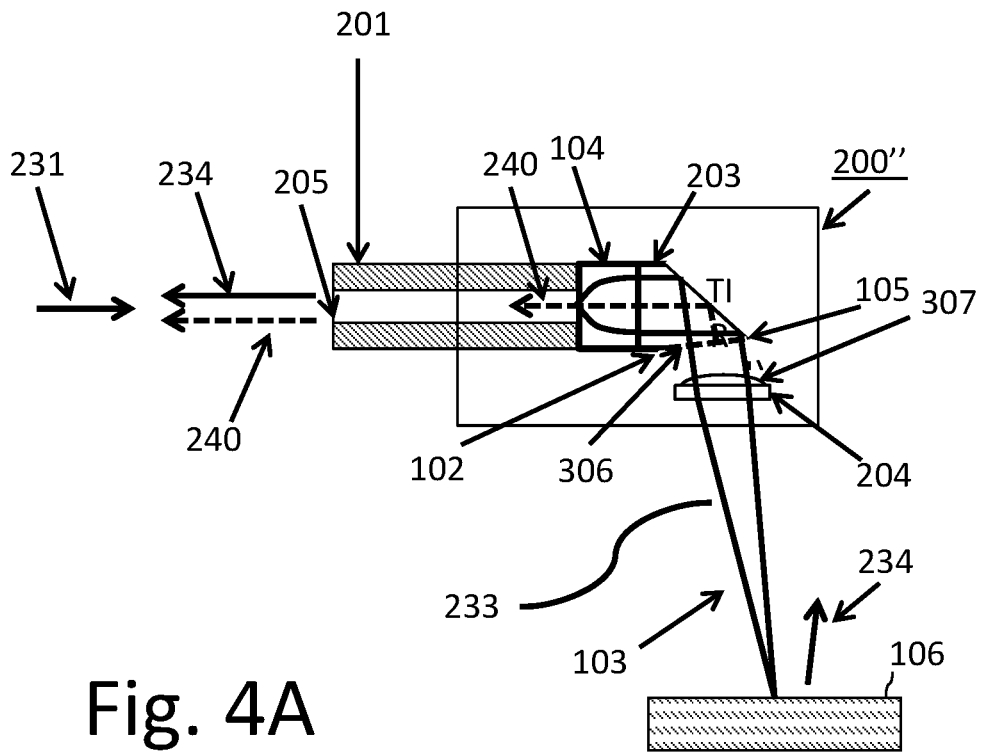
FIG. 4A is a diagram showing yet a further embodiment of a common path probe having a reference reflection disposed in or on a second polished lateral surface where the second polished surface is angle polished to be normal to an optical axis and having a lens for use with at least one OCT device or system in accordance with one or more aspects of the present disclosure.

In accordance with at least a further aspect of the present disclosure, one or more alternative embodiments of the system 100 may include a probe 200'' having the same configuration as that shown in FIG. 3A with the following exceptions (as shown in FIG. 4A): (i) the reference reflection surface 105 is disposed in an angled or tilted portion of the second lateral surface 306 of the NCF 203; and (ii) the lens 204 is on axis and is either normal (or substantially normal) to the optical axis or is parallel (or substantially parallel) to the long (longitudinal) axis of the probe 200" (e.g., an axis extending through the probe 200" along the length of the probe, an axis extending through the probe 200" from the end of the probe 200" having the fiber 201 to through the end of the probe 200" having the NCF 203, etc.). Preferably, the reference reflection 105, and/or the side 306 having the reference reflection 105, is angle polished to be normal (or substantially normal) to the optical axis. In one or more embodiments, the angle or tilt of the reference reflection surface 105 shown in FIG. 4A may be the same angle or tilt employed or shown for the embodiment of FIG. 2A so that the reference reflection 105 is normal (or substantially normal) to the optic axis (e.g., the reference reflection is 90 degrees (at a right angle) or about 90 degrees (at about a right angle) to the optic axis).

Figure 4B:
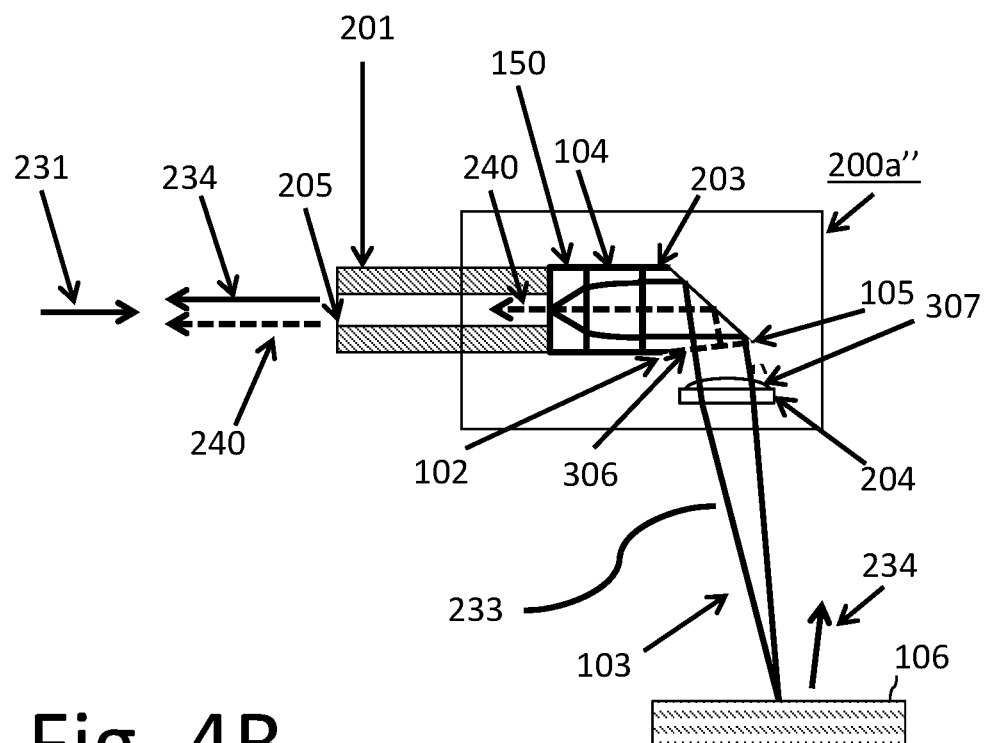
FIG. 4B is a diagram showing an alternative embodiment of the common path probe of FIG. 4A including a spacer for use with at least one OCT device or system in accordance with one or more aspects of the present disclosure.

Additionally or alternatively, as best seen in FIG. 4B, the probe 200" may further include a spacer 150 (when the probe 200" includes the spacer 150, the probe 200" may be referred to as probe 200a" to indicate such a modification from the probe 200" shown in FIG. 4A). In one or more embodiments, the spacer 150 may be useful to include, and may comprise one or more of: fused silica, a large core multimode fiber, fluid (index matching fluid) or epoxy with a specific index of refraction or the like.

Figure 5A:
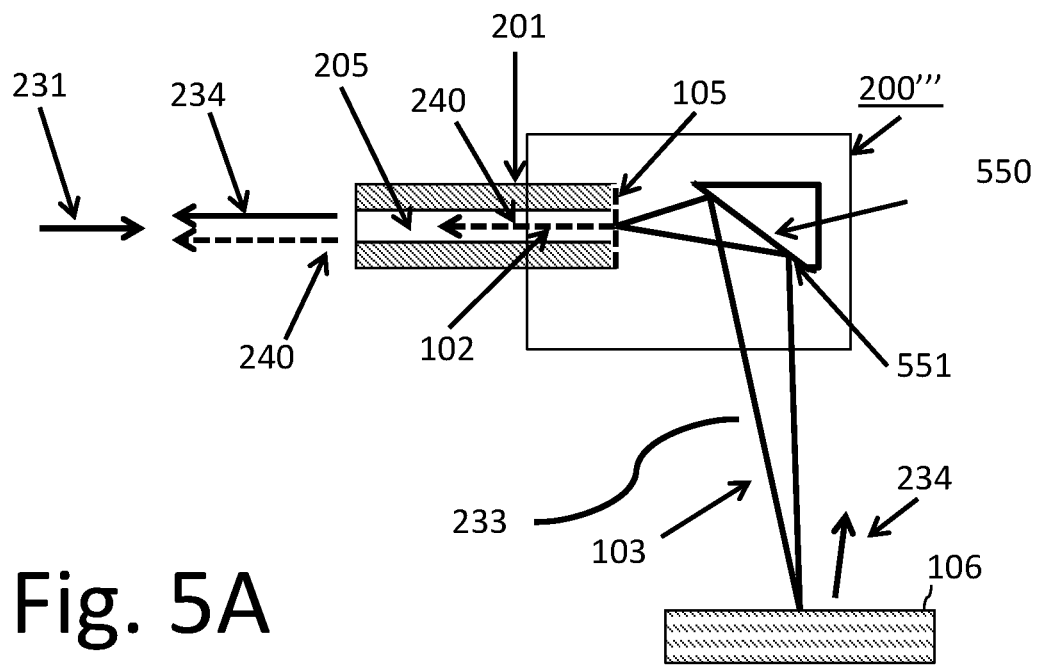
FIG. 5A is a diagram showing yet a further embodiment of a common path probe having a reference reflection disposed at an end of an optical fiber for use with at least one OCT device or system in accordance with one or more aspects of the present disclosure.

As best shown in FIG. 5A, in one or more alternative embodiments, the reference reflection 105 may be positioned at an end, end face or end surface of a fiber 201 in a probe 200'''. Alternatively to using the collimator 104 and the fiber 203, the probe 200''' includes a reflecting substrate 550 having a reflecting surface 551 thereon for reflecting light passing through the reference reflection 105 along the sample arm 103 towards the sample 106. The reflecting surface 551 may be at least one of: (i) a dielectric or a metal mirror or reflector; and (ii) flat or curved for astigmatism correction. The reflecting substrate 550 may include one or more suitable materials, such as, but not limited to, glass, injection molded plastic, epoxy, metal, etc.

Figure 5B:
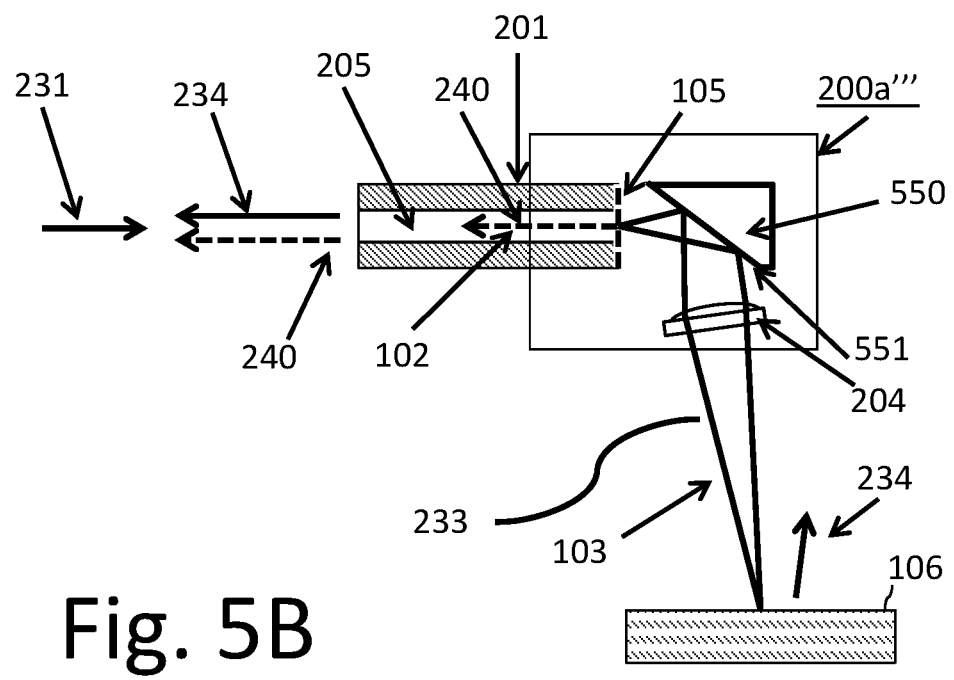
FIG. 5B is a diagram showing an alternative embodiment of the common path probe of FIG. 5A including a lens for use with at least one OCT device or system in accordance with one or more aspects of the present disclosure.

Additionally or alternatively, as shown in FIG. 5B, the probe 200''' may further include the lens 204, which receives the light reflecting off of the reflecting surface 551 of the reflecting substrate 550 and passes the light therethrough along the sample arm 103 towards the sample 106. After illuminating the sample 106, the light 234 passes through the lens 204 back towards the reflecting surface 551 of the reflecting substrate 550 and into the fiber 201. In one or more embodiments, the lens 204 may or may not be tilted or angled.

Figure 6:
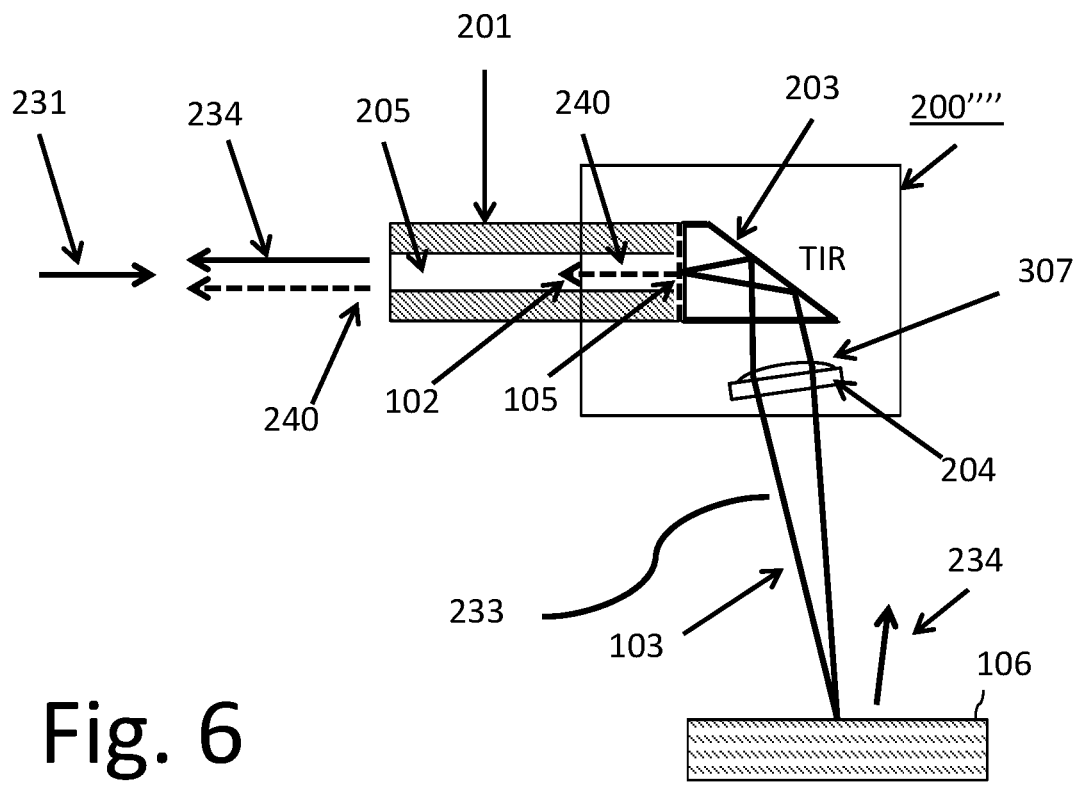
FIG. 6 is a diagram showing yet a further embodiment of a common path probe having a reference reflection disposed between an end of an optical fiber and a no core or large core multimode fiber or prism for use with at least one OCT device or system in accordance with one or more aspects of the present disclosure.

As best shown in FIG. 6, in one or more alternative embodiments, the reference reflection 105 may be positioned at an end, end face or end surface of a fiber 201 in a probe 200'''' such that the reference reflection 105 is located between the end of the fiber 201 and the fiber or prism 203. The probe 200'''' may include the lens 204, which receives light from the fiber or prism 203 and passes the light therethrough along the sample arm 103 towards the sample 106. After illuminating the sample 106, the light 234 passes through the lens 204 back towards the fiber or prism 203 and into the fiber 201. In one or more embodiments, the lens 204 may or may not be tilted or angled.

Unless otherwise discussed herein, like numerals indicate like elements. For example, while variations or differences exist between the probes 200, 200a, 200', 200a', 200", 200a", 200''', 2008''', 200'''', one or more features thereof may be the same or similar to each other, such as, but not limited to, the fiber 201 or other component(s) thereof. Those skilled in the art will appreciate that the probe 200, and/or one or more elements thereof (e.g., the collimator 104; the NCF 203; the lens 204; the reference arm 102; the sample arm 103; etc.), may operate in the same or similar fashion to the probes 200a, 200', 200a', 200", 200a", and/or those like-numbered elements of the probes 200a, 200', 200a', 200", 200a" as discussed above or any additional like-numbered elements discussed further herein below. Those skilled in the art will appreciate the other alternative embodiments of probes 200''', 200a''', 200'''', and/or one or more like-numbered elements thereof (e.g., the fiber 201, the reference arm 102, the sample arm 103, etc.), while having other variations as discussed herein, may operate in the same or similar fashion to the like-numbered elements of any of the other probes discussed herein, such as, but not limited to, the probes 200, 200a, 200', 200a', 200", 200a". Indeed, while certain differences exist between the probes 200, 200a, 200', 200a', 200", 200a", 200''', 200a''', 200'''' as aforementioned, there are many similarities between the probes 200, 200a, 200', 200a', 200", 200a", 200''', 200a''', 200''''.

In one or more embodiments including the adjustment section 140, the deflected section 108 also operates to pass the light from the common path probe or probe housing 200 to the adjustment section 140 and towards the at least one detector 107 (via the adjustment section 140). The adjustment section 140 may control relative optical characteristics between the reference beam 240 and the sample beam 234.

In accordance with at least one aspect of the present disclosure, a feature of common path OCT systems is implemented using fiber optics. As aforementioned, one application of a common path OCT technique of the present disclosure is to use with the catheter, such as catheter 520 schematically shown in FIG. 7. FIG. 7 shows an embodiment of the catheter 520 including a sheath 521, a coil 522, a protector 523 and an optical probe 524. The catheter 520 preferably is connected to the system via a connection component or interface module as described above, such as, but not limited to, a rotary junction. The coil 522 delivers torque from a proximal end to a distal end thereof. In one or more embodiments, the coil 522 is fixed with/to the optical probe 524 so that a distal tip of the optical probe 524 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in any of FIGS. 1-4) of an OCT deflection section or interference system (e.g., an OCT interferometer) in order to provide access to internal organs, such as intravascular images, gastro-intestinal tract or any other narrow area, that are difficult to access. As the beam of light through the optical probe 524 inside of the catheter 520 or endoscope is rotated across the surface of interest, cross-sectional images of one or more samples (such as the sample 106) are obtained. In order to acquire three-dimensional data, the optical probe 524 is simultaneously translated longitudinally during the rotational spin resulting in a helical scanning pattern. This translation is most commonly performed by pulling the tip of the probe 524 back towards the proximal end and therefore referred to as a pullback.

In accordance with another aspect of the present disclosure and as aforementioned, one or more methods for performing common path OCT are provided herein. FIG. 8 illustrates a flow chart of at least one embodiment of a method for performing common path OCT. Preferably, the method(s) may include one or more of the following: (i) positioning a reference reflection (such as the reference reflection 105) in the collimation field or path (step S8000 of FIG. 8); and (ii) positioning a reference reflection (such as the reference reflection 105) such that it is normal (or substantially normal) to the optic axis (step S8001 of FIG. 8). Alternatively or additionally, the reference reflection 105 may be positioned to have an angle with respect to the optic axis of at least one of the following: ±a few degrees from normal or substantially normal, normal, substantially normal, about 87 degrees to about 93 degrees, about 88 degrees to about 92 degrees, about 89 degrees to about 91 degrees, and any other angle or range of angles that would improve coupling efficiency.

In one or more embodiments of an interferometer (e.g., a Michelson interferometer), a light source, such as the light source 101, operates to produce a light to a splitter, which splits the light from the light source 101 into a reference beam passing into a reference arm and a sample beam passing into a sample arm, which are typically physically separate arms. In such an interferometer, a deflection section (such as the deflection section 108, which may be a beam splitter or other suitable component as described hereinabove) is positioned or disposed at an angle to a reference mirror (such as the reference mirror 105), at least one detector (such as the detector 107) and to a sample (such as the sample 106). The reference beam is reflected from a reference mirror (such as the reference reflection 105) in the reference arm while the sample beam is reflected or scattered from a sample (such as the sample 106) in the sample arm. Both of the reference and sample beams couple, combine, or recombine at the deflection section (and/or an adjustment section 140 as described above) and generate interference patterns.

In accordance with one or more additional aspects of the present disclosure, common path probes, such as the probes 200, 200a', 200', 200a', 200", 200a", 200''', 200a''', 200'''' may be utilized to achieve phase noise reduction. Phase noises may be added while spinning a fiber probe, such as the optical probe 524 (shown in FIG. 7). As such, common path probes may be utilized to reduce such phase noises. To separate the reference and sample arms 102, 103 (see e.g., FIGS. 2A-6) with a common path probe, double interferometers may be applied. FIG. 9 illustrates a schematic interferometer for use with a common path probe (such as, but not limited to, the probes 200, 200a, 200', 200a', 200", 200a", 200''', 200a''', 200'''') in accordance with the present disclosure. A light source 101 operates to deliver light into a common path probe (e.g., the probe 200, 200a, 200', 200a', 200", 200a", 200''', 200a''', 200'''') via a circulator 901, a deflection section 108 and, in one or more embodiments, a patient user or interface unit or device ("PIU") 110. By way of at least one embodiment example where the deflection section 108 is a beam splitter, both a reference beam and a sample beam go back to the splitter 108 from the common path probe (such as the probe 200) through the PIU 110. The beams are split and go to the circulator 901 and circulator 902. The beam via the circulator 901 delivers to a combiner 903. The beam via the circulator 902 may go to a phase shift unit 130 (which may include a reference mirror in one or more embodiments and may operate to apply phase modulation in the reference beam.) via a length adjustment section 904 of the reference arm (e.g., reference arm 103), and then the beam goes to the combiner 903. The combiner 903 combines both beams via the circulator 901 and the circulator 902, and the combined beams are delivered to one or more detectors (such as the one or more detectors 107). Alternatively, in one or more embodiments, the beams via the circulators 901, 902 may go to the adjustment section 140 as described above, and then to the at least one detector 107. The reference beam is reflected at a distal end of the common path probe (such as the probe 200, 200a, 200', 200a', 200", 200a", 200''', 200a''', 200'''', etc.). Therefore, both the sample and reference beams go through the optical probe (such as the probe 200, 200a, 200', 200a', 200", 200a", 200''', 200a''', 200'''', etc.), which make phase noises from an optical fiber canceled or reduced as aforementioned.

An optical probe distance between the reference optical path length and sample optical path length in the optical probe is approximately same as the distance between optical path 1 and optical path 2. Optical path 1 is an optical path length from the splitter (or deflection section) 108 to the combiner 903 via the circulator 901. Optical path 2 is the path length from the splitter (or deflection section) 108 to the combiner 903 via the circulator 902. When the reference optical path length is longer than the sample optical path length, optical path 1 is longer than optical path 2. When the reference optical path length is shorter than the sample optical path length, optical path 1 is shorter than optical path 2.

There are many ways to compute power, digital as well as analog. In at least one embodiment, a computer may be dedicated to the control and the monitoring of the OCT devices, systems, methods and/or storage mediums described herein.

Figure 10:
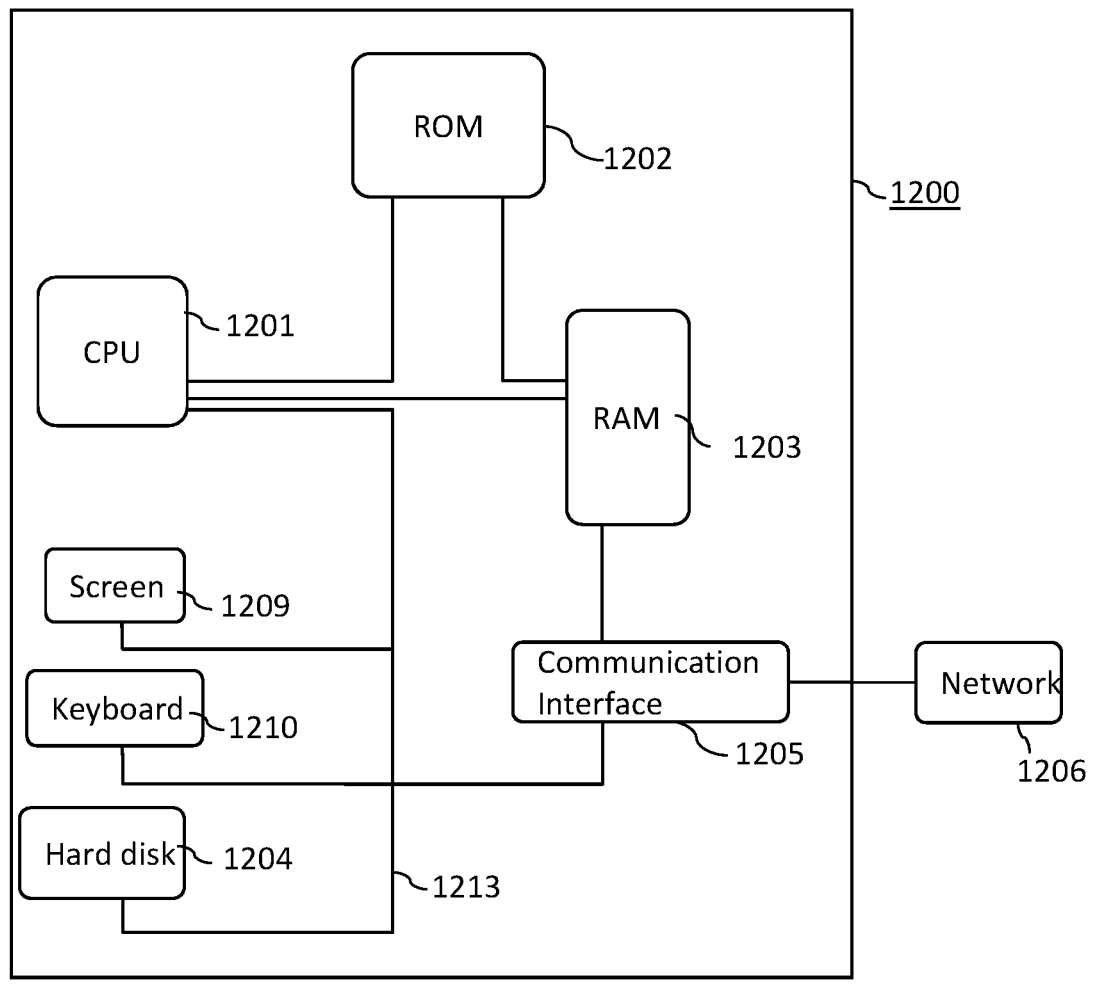
FIG. 10 shows a schematic diagram of an embodiment of a computer that may be used with one or more embodiments of a common path OCT technique(s) in accordance with one or more aspects of the present disclosure.

Various components of a computer system 1200 are provided in FIG. 10. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 10). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a common path system, such as the system 100 discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for common path OCT imaging. The system 1200 may further include one or more processors connected via a network connection (e.g., via network 1206). The CPU 1201 and any additional processor being used by the system 1200 may be located in the same telecom network or in different telecom networks (e.g., performing common path OCT may be controlled remotely).

The I/O or communication interface 1205 provides communication interfaces to input and output devices, which may include the light source 101, a spectrometer, a microphone, a communication cable and a network (either wired or wireless), a keyboard 1210, a mouse, a touch screen or screen 1209, a light pen and so on. The Monitor interface or screen 1209 provides communication interfaces thereto.

Any methods and/or data of the present disclosure, such as the methods for performing common path OCT as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 10. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 10) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components. Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

The present disclosure and/or one or more components of devices, systems and storage mediums, and/or methods, thereof also may be used in conjunction with any suitable optical assembly including, but not limited to, arrangements and methods for providing multimodality microscopic imaging of one or more biological structure, such as those disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures in U.S. Patent Publication Nos. 2012/0101374 and 2009/0192358, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. A common path optical coherence tomography system, the system comprising:
   a common path interference optical system that operates to:
   (i) receive light from a light source,
   (ii) send the light along a reference arm of the common path interference optical system to a reference reflection of the common path interference optical system, the reference reflection operating to divide the light into a first light with which an object or sample is to be irradiated and which passes through the reference reflection and travels along a sample arm of the common path interference optical system, and to divide the light into a second reference light reflected off of the reference reflection of the common path interference optical system and sent back along the reference arm, the reference reflection being positioned such that: (a) the returning first light passing through the reference reflection, or a light generated from at least reflected or scattered light of the first light with which the object or sample is to be irradiated, is maximized, (b) the reference reflection defines an end of a common path for the reference arm and at least a portion of the sample arm, and (c) the reference reflection defines an end of the reference arm, and (iii) generate interference light by causing the returning first light or the at least reflected or scattered light of the first light with which the object or sample has been irradiated and the reflected second reference light to combine or recombine, and to interfere, with each other, the interference light generating one or more interference patterns, wherein the reference arm overlaps with at least the portion of the sample arm along the common path, the entire reference arm is included or positioned along the common path, and another portion of the sample arm extends away from the reference reflection and the common path;

a lens positioned after the reference reflection along the another portion of the sample arm such that the first light passes from the common path through the reference reflection, and passes through the lens, along the another portion of the sample arm; and at least one detector that operates to continuously acquire the interference light to measure the interference or the one or more interference patterns between the combined or recombined light, wherein:

(i) the reference reflection is positioned at an end of a common path fiber or outside of the common path fiber, and the reference reflection is positioned in a path of the light such that the reference reflection is perpendicular or substantially perpendicular to an optic axis of the light;

(ii) the lens is positioned off axis with respect to an axis extending through or along a length of the common path fiber; and (iii) the common path interference optical system includes a probe having: a fiber attached to a collimator, a no core fiber (NCF) or large core multimode fiber, and the lens, wherein the lens is in communication with the reference reflection or the lens has the reference reflection disposed on the lens, and wherein one or more of the following is/are met:

(a) the fiber attached to the collimator operates as a signal carrying optical fiber;

(b) the fiber attached to the collimator comprises: a single mode fiber (SMF), a double clad fiber (DCF), or a multimode fiber; and/or (c) the common path fiber is included in, or is part of, the fiber attached to the collimator.

2. The common path optical coherence tomography system according to claim 1, wherein one or more of the following is/are met:

(i) the probe further includes a spacer positioned between the fiber and the collimator, the spacer operating to further broaden the light beam or beams;

(ii) the spacer comprises at least one of: fused silica, a large core multimode fiber, fluid, an index matching fluid, and an epoxy with a specific index of refraction;

(iii) the probe is positioned in a sheath;

(iv) the collimator is a collimating gradient index (GRIN) lens or fiber that is fusion spliced to the fiber;

(v) the NCF or large core multimode fiber is fusion spliced to the collimator comprising a GRIN lens or fiber;

(vi) the NCF or large core multimode fiber is polished at an angle that meets a total internal reflection (TIR) condition and is larger than 45 degrees or larger than about 45 degrees so as to reduce or minimize undesired reflection(s) from a side surface of the NCF or large core multimode fiber;

(vii) the lens includes an astigmatism to correct or compensate for use of the sheath; and/or (viii) the lens is spaced away and separate from the common path fiber.

3. The common path optical coherence tomography system according to claim 1, wherein one or more of the following is/are met:

(i) the lens includes a curved surface that operates to interact with the light passing through the lens and that reduces one or more aberrations;

(ii) the reference reflection is disposed on or is in communication with a first side of the lens, and the curved surface is disposed on a second side of the lens such that the curved surface is positioned in between the lens and the object or sample; and/or (iii) the lens is spaced away and separate from the common path fiber.

4. The common path optical coherence tomography system according to claim 1, wherein one or more of the following is/are met:

(i) the reference reflection comprises an anti-reflective (AR) coating, a high reflection (HR) coating, or a partial mirror; and/or (ii) the reference reflection allows for an improved or maximized signal-to-noise ratio (SNR) compared to an SNR of a configuration not using the reference reflection.

5. The common path optical coherence tomography system according to claim 1, further comprising one or more of the following:

(i) the light source that operates to produce the light; and/or (ii) a guide or waveguide for transmitting the light from the light source.

6. The common path optical coherence tomography system according to claim 1, further comprising a deflecting section that operates to deflect the light from the light source to the common path interference optical system, and then send light received from the common path interference optical system towards the at least one detector.

7. The common path optical coherence tomography system according to claim 6, wherein the deflecting section comprises one or more of the following: one or more common path interferometers, a circulator, a beam splitter, an isolator, a coupler, a fusion fiber coupler, a partially severed mirror with holes therein, and/or a partially severed mirror with a tap.

8. The common path optical coherence tomography system according to claim 6, wherein the reference arm and the sample arm overlap or share the common path between the deflecting section and the reference reflection.

9. The common path optical coherence tomography system according to claim 6, further comprising an adjustment section that operates to control one or more relative optical characteristics between the first light having illuminated the object or sample and the reflected second light, wherein the deflecting section further operates to pass the light from the probe to the adjustment section and towards the at least one detector.

10. The common path optical coherence tomography system according to claim 1, wherein the reference reflection:

(i) includes an optical coating to improve or optimize a reflection value for the reference reflection compared to a situation where the reference reflection is not using the optical coating; or (ii) is additionally angled to improve or optimize the second reference light or a signal therefor compared to a situation where the additional angle is not used.

11. The common path optical coherence tomography system according to claim 1, wherein one or more of the following is/are met:
   (i) the reference reflection interacts with the light such that the light travels along the same path along which the light arrived to the reference reflection; and/or
   (ii) the common path OCT system includes a reflector, the reflector operating to totally reflect the first light to and/or from the reference reflection.

12. The common path optical coherence tomography system according to claim 1,
   wherein the reference reflection:
   (i) forms a first portion of the lens such that the first portion having the reference reflection is located or disposed between the fiber and a remaining second portion of the lens; or
   (ii) forms a first portion of the lens such that the first portion having the reference reflection is located or disposed between the fiber and a remaining second portion of the lens, the lens being spaced away from the collimator and/or the NCF or large core multimode fiber.

13. The common path optical coherence tomography system according to claim 12, wherein:
   the reference reflection is tilted at a predetermined angle, the predetermined angle being one or more of the following: 1-3 degrees, 0-2 degrees, about 1 degree to about 3 degrees, and about 0 degrees to about 2 degrees.

14. A method for performing common path optical coherence tomography ("OCT") using a common path OCT device or system having a common path interference optical system that operates to generate interference light and one or more interference patterns from a light that has been split into a first light with which an object or sample has been irradiated via a portion of a sample arm of the common path interference optical system and a second reference light, which travels along a reference arm of the common path interference optical system, and having at least one detector, the method comprising:
   positioning a reference reflection of the common path interference optical system such that (i) the position of the reference reflection is configured to maximize the returning first light passing through the reference reflection, or to maximize a light generated from at least reflected or scattered light of the first light with which the object or sample has been irradiated, (ii) the reference reflection defines an end of a common path for the reference arm and a portion of the sample arm, and (iii) the reference reflection defines an end of the reference arm,
   wherein the reference arm overlaps with at least the portion of the sample arm along the common path, the entire reference arm is included or positioned along the common path, and another portion of the sample arm extends away from the reference reflection and the common path,
   wherein the common path OCT device or system further includes a lens positioned after the reference reflection along the another portion of the sample arm such that the first light passes from the common path through the reference reflection, and passes through the lens, along the another portion of the sample arm, and wherein:
   (i) the reference reflection is positioned at an end of a common path fiber or outside of the common path fiber, and the reference reflection is positioned in a path of the light such that the reference reflection is perpendicular or substantially perpendicular to an optic axis of the light;
   (ii) the lens is positioned off axis with respect to an axis extending through or along a length of the common path fiber; and
   (iii) the common path interference optical system includes a probe having: a fiber attached to a collimator, a no core fiber (NCF) or large core multimode fiber, and the lens, wherein the lens is in communication with the reference reflection or the lens has the reference reflection disposed on the lens, and wherein one or more of the following is/are met:
      (a) the fiber attached to the collimator operates as a signal carrying optical fiber;
      (b) the fiber attached to the collimator comprises: a single mode fiber (SMF), a double clad fiber (DCF), or a multimode fiber; and/or
      (c) the common path fiber is included in, or is part of, the fiber attached to the collimator.

15. The method of claim 14, further comprising sending the light along the reference arm of the common path interference optical system to the reference reflection of the common path interference optical system, the reference reflection operating to divide or split the light into the first light, which passes through the reference reflection, and the second reference light, which reflects off of the reference reflection and sent back along the reference arm.

16. The method of claim 14, further comprising positioning the reference reflection in a collimation field or path of the common path interference optical system.

17. The method of claim 14, further comprising:
   (i) generating the interference light by causing the returning first light or the at least reflected or scattered light of the first light with which the object or sample has been irradiated and the reflected second reference light to combine or recombine, and to interfere, with each other, the interference light generating one or more interference patterns; and
   (ii) acquiring, via the at least one detector, the interference light and/or the one or more interference patterns to measure the interference or the one or more interference patterns.

18. The method of claim 14, wherein one or more of the following is/are met:
   (i) the reference reflection interacts with the light such that the light travels along the same path along which the light arrived to the reference reflection; and/or
   (ii) the common path optical coherence tomography system includes a reflector, the reflector operating to totally reflect the first light to and/or from the reference reflection.

19. The method of claim 14,
   wherein the reference reflection:
   (i) forms a first portion of the lens such that the first portion having the reference reflection is located or disposed between the fiber and a remaining second portion of the lens; or
   (ii) forms a first portion of the lens such that the first portion having the reference reflection is located or disposed between the fiber and a remaining second portion of the lens, the lens being spaced away from the collimator and/or the NCF or large core multimode fiber.

20. The method of claim 19, wherein:
the reference reflection is tilted at a predetermined angle, the predetermined angle being one or more of the following: 1-3 degrees, 0-2 degrees, about 1 degree to about 3 degrees, and about 0 degrees to about 2 degrees.

\* \* \* \* \*